United States Patent
Lee et al.

(10) Patent No.: US 9,789,878 B2
(45) Date of Patent: Oct. 17, 2017

(54) DRIVER REST RECOMMENDATION

(71) Applicant: LG ELECTRONICS INC., Seoul (KR)

(72) Inventors: Kiho Lee, Seoul (KR); Hyeoncheol Lee, Seoul (KR); Jaehee Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 14/690,716

(22) Filed: Apr. 20, 2015

(65) Prior Publication Data
US 2016/0046294 A1    Feb. 18, 2016

Related U.S. Application Data

(60) Provisional application No. 61/983,895, filed on Apr. 24, 2014.

(30) Foreign Application Priority Data

Jun. 13, 2014    (KR) ........................ 10-2014-0072233

(51) Int. Cl.
*B60R 25/10*    (2013.01)
*B60Q 1/00*    (2006.01)
(Continued)

(52) U.S. Cl.
CPC ............... *B60W 40/08* (2013.01); *A61B 5/18* (2013.01); *B60K 28/06* (2013.01); *G06F 3/016* (2013.01);
(Continued)

(58) Field of Classification Search
CPC ......... G08B 21/06; A61B 5/18; A61B 5/0205; B60K 28/06; B60K 28/066
See application file for complete search history.

(56) References Cited

U.S. PATENT DOCUMENTS 6,009,403 A * 12/1999 Sato ..................... G01C 21/343
                                                        340/990
6,239,707 B1 * 5/2001 Park ......................... A61B 5/18
                                                        340/573.1
(Continued)

FOREIGN PATENT DOCUMENTS

CN            101035705        9/2007
EP         1 291 226 A2        3/2003
(Continued)

OTHER PUBLICATIONS

European Search Report dated Sep. 29, 2015 for EP Patent Application No. 15001173.2, 7 pages.
(Continued)

*Primary Examiner* — Steven Lim
*Assistant Examiner* — Muhammad Adnan
(74) *Attorney, Agent, or Firm* — Fish & Richardson P.C.

(57) ABSTRACT

Methods and systems for monitoring a driver of a vehicle using a driver state monitoring (DSM) system. The DSM system includes a sensing unit that senses biological information of a user of a vehicle. The DSM system also includes a controller that determines a drowsy state of the user based on the sensed biological information. The controller also determines a current condition of traffic and outputs information recommending rest for the user based on the determined drowsy state of the user and the determined current condition of traffic. The controller monitors the traffic and determines a rest state of the user, and outputs an alarm based on monitoring the traffic and the determined rest state of the user.

20 Claims, 7 Drawing Sheets

(51) Int. Cl.

| | | |
|---|---|---|
| G08B 23/00 | (2006.01) | |
| G08B 13/00 | (2006.01) | |
| B60R 21/26 | (2011.01) | |
| A61B 5/00 | (2006.01) | |
| A61B 5/04 | (2006.01) | |
| B60W 40/08 | (2012.01) | |
| A61B 5/18 | (2006.01) | |
| B60K 28/06 | (2006.01) | |
| G08B 21/06 | (2006.01) | |
| G06F 3/01 | (2006.01) | |
| A61B 5/024 | (2006.01) | |
| G06F 3/0354 | (2013.01) | |

(52) U.S. Cl.
CPC .......... G08B 21/06 (2013.01); *A61B 5/02438* (2013.01); *A61B 5/4812* (2013.01); *A61B 5/681* (2013.01); *B60W 2040/0827* (2013.01); *G06F 3/03547* (2013.01); *G06F 2203/011* (2013.01)

(56) References Cited

U.S. PATENT DOCUMENTS

| | | | | |
|---|---|---|---|---|
| 6,265,978 | B1* | 7/2001 | Atlas | G08B 21/06 340/573.1 |
| 6,853,896 | B2* | 2/2005 | Akiyama | B60R 25/00 340/439 |
| 7,038,596 | B2* | 5/2006 | Nakajima | G08G 1/096725 340/439 |
| 7,202,792 | B2* | 4/2007 | Zhang | G08B 21/06 340/436 |
| 7,349,782 | B2* | 3/2008 | Churchill | G08G 1/164 340/438 |
| 7,565,230 | B2* | 7/2009 | Gardner | G09B 9/052 180/272 |
| 9,135,803 | B1* | 9/2015 | Fields | B60K 28/066 |
| 2002/0004700 | A1* | 1/2002 | Klein | G01C 21/343 701/532 |
| 2002/0053153 | A1* | 5/2002 | Nesbitt | G09F 15/0037 40/607.03 |
| 2003/0218321 | A1* | 11/2003 | Suzuki | B60N 2/002 280/730.1 |
| 2004/0051642 | A1* | 3/2004 | Choi | G08B 21/06 340/575 |
| 2005/0114014 | A1* | 5/2005 | Isaac | G01C 21/26 701/465 |
| 2006/0190822 | A1* | 8/2006 | Basson | G06Q 10/10 715/700 |
| 2007/0008151 | A1* | 1/2007 | Victor | A61B 5/11 340/573.1 |
| 2007/0017531 | A1* | 1/2007 | Large | A61B 5/103 128/898 |
| 2007/0296601 | A1* | 12/2007 | Sultan | A61B 5/18 340/576 |
| 2008/0228400 | A1* | 9/2008 | Wheeler | G08G 1/02 701/301 |
| 2008/0291032 | A1* | 11/2008 | Prokhorov | B60K 28/066 340/576 |
| 2009/0209829 | A1* | 8/2009 | Yanagidaira | A61B 5/165 600/301 |
| 2011/0043350 | A1* | 2/2011 | Ben David | B60Q 9/00 340/441 |
| 2012/0306637 | A1* | 12/2012 | McGough | B60K 37/06 340/439 |
| 2013/0088369 | A1* | 4/2013 | Yu | B60W 40/09 340/905 |
| 2013/0113910 | A1* | 5/2013 | Kim | B60K 28/066 348/77 |
| 2013/0194099 | A1* | 8/2013 | Nagata | B60K 28/06 340/575 |
| 2013/0218971 | A1* | 8/2013 | Sasaki | H04W 4/00 709/204 |
| 2013/0226408 | A1* | 8/2013 | Fung | B60W 40/09 701/41 |
| 2014/0077957 | A1* | 3/2014 | Bichara | G08B 21/06 340/575 |
| 2014/0107493 | A1* | 4/2014 | Yuen | H04W 4/027 600/473 |
| 2014/0275834 | A1* | 9/2014 | Bennett | B60N 2/502 600/301 |
| 2014/0350830 | A1* | 11/2014 | David | G08G 1/0116 701/117 |
| 2015/0193885 | A1* | 7/2015 | Akiva | G06Q 40/08 705/4 |
| 2015/0338917 | A1* | 11/2015 | Steiner | H04L 9/3231 345/156 |

FOREIGN PATENT DOCUMENTS

| | | | |
|---|---|---|---|
| EP | 2 605 228 A2 | | 6/2013 |
| JP | 2008-299529 A | | 12/2008 |
| JP | 2009-213711 A | | 9/2009 |
| JP | 2011052979 A | * | 3/2011 |
| JP | 4812750 B2 | | 11/2011 |
| JP | 2011-248850 A | | 12/2011 |
| JP | 2010-082377 A | | 6/2012 |
| JP | 2014071628 A | * | 4/2014 |
| WO | 2006037696 | | 4/2006 |
| WO | WO 2006/098181 A1 | | 9/2006 |

OTHER PUBLICATIONS

European Search Report dated Oct. 19, 2015 for EP Patent Application No. 15001196.3, 5 pages.
Korean Office Action dated Jul. 3, 2015 for Korean Application No. 10-2014-00072233, 7 Pages.
Chinese Office Action in Chinese Application No. 201510201453.5, dated Dec. 27, 2016, 19 pages (with English translation).
Chinese Office Action in Chinese Application No. 201510201512.9, dated Dec. 27, 2016, 17 pages (with English translation).

* cited by examiner

DRIVER REST RECOMMENDATION

CROSS-REFERENCE TO RELATED APPLICATIONS

This application claims, pursuant to 35 U.S.C. §119(e), the benefit of U.S. Provisional Application No. 61/983,895 filed on Apr. 24, 2014 and, pursuant to 35 U.S.C. §119(a), the benefit of Korean Application No. 10-2014-0072233, filed on Jun. 13, 2014, the contents of which are incorporated by reference herein in their entirety.

TECHNICAL FIELD

This application relates to vehicle control based on monitoring a driver drowsiness condition and traffic conditions.

BACKGROUND

Wearable devices include various types of electronic devices that a user can wear on a user's body or clothes. The wearable devices may be, for example, a smart watch, a wearable computer, smart glasses, a headset, other smart wear, and the like.

SUMMARY

In one aspect, a driver state monitoring (DSM) system includes a sensing unit configured to sense biological information of a user of a vehicle. The DSM system also includes a controller configured to determine a drowsy state of the user based on the sensed biological information and to determine a current condition of traffic. The controller is configured to output information recommending rest for the user based on the determined drowsy state of the user and the determined current condition of traffic. The controller is further configured to monitor the traffic and determine a rest state of the user, and output an alarm based on monitoring the traffic and the determined rest state of the user.

In some embodiments, the controller is further configured to determine a driving time to the destination, and providing output information recommending rest for the user is based on the driving time and the current condition of the traffic.

In some embodiments, the controller is further configured to detect that the user is in the rest state; determine an updated condition of the traffic; and change an alarm output time based on the updated condition of the traffic.

In some embodiments, the controller is further configured to, based on analyzing the updated condition of the traffic, determine the alarm output time based on determining that the traffic has improved above a predetermined level.

In some embodiments, the controller is further configured to re-sense the biological information of the user based on determining that the traffic has changed as a result of analyzing the updated conditions of the traffic; and determine the alarm output time based on the re-sensed biological information.

In some embodiments, the controller is further configured to re-sense the biological information of the user based on the output of the alarm; and output updated information recommending rest for the user based on a result of re-sensing the biological-information of the user.

In some embodiments, the updated information recommending rest for the user further includes information associated with an updated drowsy state of the user determined based on the re-sensed biological information of the user.

In some embodiments, the biological information is associated with the user's heartbeat spectrum, and the controller is further configured to classify the rest state of the user as any one of a plurality of sleep stages based on a result of analyzing the heartbeat spectrum.

In some embodiments, the controller is further configured to determine a time for outputting the alarm based on the classified sleep stage.

In some embodiments, the controller is further configured to, based on determining the information recommending rest for the user, change an environment inside the vehicle according to preset vehicle environment setting information. The preset vehicle environment setting information is preset to induce the user to sleep, and is associated with at least one of illumination, aroma, or ventilation inside the vehicle.

In some embodiments, the controller is further configured to determine a first arrival time to a destination based on the current condition of the traffic; determine a second condition of the traffic; determine a second arrival time to the destination based on the second condition of the traffic; and generate the information recommending rest for the user based on comparing the first arrival time with the second arrival time.

In some embodiments, the controller is further configured to determine an estimated driving time to the destination based on the user resting until a scheduled time at which the alarm is output; and determine the information recommending rest based on the estimated driving time.

In some embodiments, the wearable device is configured to be linked with the vehicle, and the controller is further configured to output the information recommending rest for the user on at least one of a display unit of the wearable device or an information display device provided in the vehicle.

In some embodiments, the controller is further configured to output the alarm by outputting at least one of image information, an audible sound, or a vibration.

In some embodiments, the second condition of the traffic has less traffic congestion than the current condition of the traffic.

In some embodiments, the controller is further configured to determine the current condition of the traffic at a plurality of times while the vehicle is being driven to the destination; and to determine the second arrival time based on determining the current condition of the traffic at the plurality of times.

In some embodiments, the controller is further configured to, based on determining that the user is in a sleep state, determine a time for outputting the alarm based on a time specified in a preset schedule and based on a driving time to the destination.

In some embodiments, the controller is further configured to, based on determining that the user is in a sleep state, determine whether the user is able to arrive at the destination by the time specified in the preset schedule according to the current condition of the traffic; determine contact information associated with the preset schedule; and transmit a message using the contact information.

In some embodiments, the controller is further configured to determine a time for outputting the alarm based on a preset light sleep time.

In another aspect, a control method of a DSM system includes sensing biological information of a user of a vehicle, and determining a drowsy state of the user based on the sensed biological information. The method also includes determining a current condition of traffic, and outputting information recommending rest for the user based on the determined drowsy state of the user and the determined current condition of traffic. The method further includes monitoring the traffic and determining a rest state of the user; and outputting an alarm based on monitoring the traffic and the determined rest state of the user.

All or part of the features described throughout this application can be implemented as a computer program product including instructions that are stored on one or more non-transitory machine-readable storage media, and that are executable on one or more processing devices. All or part of the features described throughout this application can be implemented as an apparatus, method, or electronic system that can include one or more processing devices and memory to store executable instructions to implement the stated functions.

The details of one or more implementations are set forth in the accompanying drawings and the description below. Other features will be apparent from the description and drawings, and from the claims. The description and specific examples below are given by way of illustration only, and various changes and modifications will be apparent.

DETAILED DESCRIPTION

Figure 1:
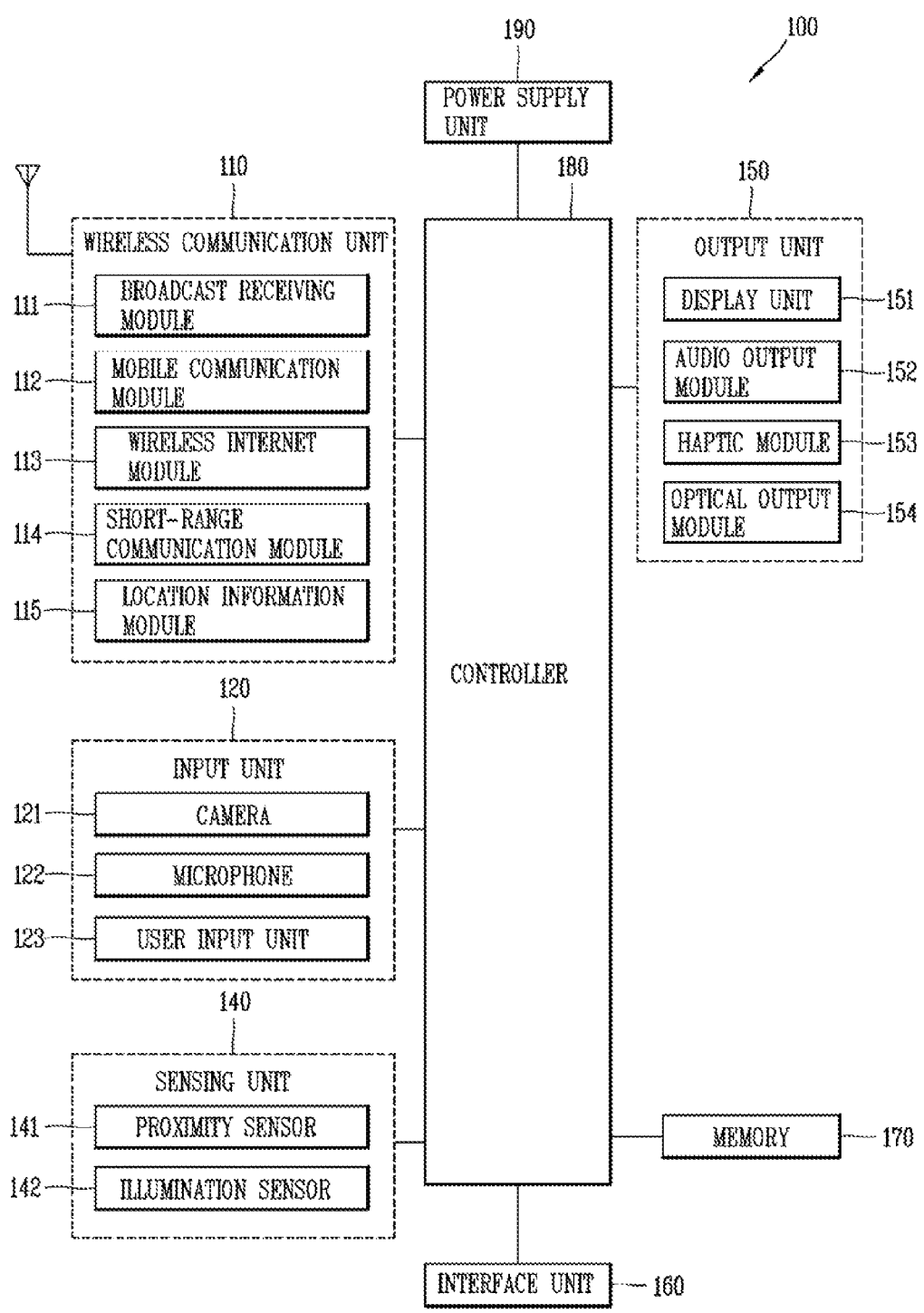
FIG. 1 is a block diagram illustrating an example of a wearable device.

In some scenarios, a driver of vehicle can face a dilemma of being physically tired but having to reach a destination in a timely manner. In such scenarios, the driver may continue driving despite being tired, endangering not only the driver but others. The driver may continue driving in a tired condition despite the fact that current and/or future traffic conditions would allow the driver to stop driving momentarily and take a rest.

A driver state monitoring (DSM) system is configured to help a driver avoid such dangerous situations by generating recommendations to rest, based on the driver's biological information and based on traffic conditions. The DSM system includes a wearable device that can be worn by the user and interacts with other components of the vehicle. The system analyzes the driver's biological information as well as various factors that contribute to the driver arriving at a destination in a timely manner (e.g., traffic congestion, distance to the destination, etc.). Based on these various types of information, the DSM system generates a recommendation for whether the driver should rest, and for how long the driver should rest.

In some implementations, a driver state monitoring (DSM) system analyzes both biological information of a driver of a vehicle as well as traffic conditions along routes towards the user's destination. For example, the system can utilize data from one or more sensors that are in contact with the user's body (e.g., via a wearable device, such as a smart watch) to determine the user's biological information. The system can also utilize data regarding traffic (e.g., traffic congestion level, distance remaining until destination, navigation data, etc.) to determine current and/or future conditions of traffic. Based on both the biological information and the traffic condition, the system may generate a recommendation to the driver on how much to rest. For example, the system may output a recommendation of, "If you rest for 10 minutes now, you can still make it to your destination on time." As another example, the system may output a recommendation of, "If you rest for 10 minutes now, you will be 25 minutes late instead of 20 minutes late."

In some implementations, if the user accepts the recommendation to rest, the system may output an alarm to indicate that the user should finish resting and resume driving. For example, the system may monitor traffic conditions and also monitor the user's rest state and generate a time to output the alarm. In some implementations, the system can dynamically change the recommendation and/or the alarm, for example, based on the traffic condition getting better or worse, or based on the user's biological information indicating that the user has achieved sufficient or insufficient rest. For example, the system may initially suggest 15 minutes of rest, and based on improved traffic conditions, the system can change the recommendation and/or the alarm to add 5 more minutes of rest. As another example, after initially recommending 15 minutes of rest, the system may determine that the user has not achieved sufficient rest, and may change the recommendation and/or the alarm to add 5 more minutes of rest. As yet another example, after initially recommending 15 minutes of rest, the system may determine that the user has achieved sufficient rest and/or that traffic condition has gotten worse, and may change the recommendation and/or the alarm for 5 fewer minutes of rest. In some implementations, the system may apply weighting factors to the timeliness criteria and/or a rest criteria, and may determine the recommendation based on the weighting factors.

In some implementations, in addition or as an alternative to an alarm, the system may adjust environmental settings in the vehicle based on a recommendation of rest. For example, the system may adjust environmental settings in the vehicle to make the vehicle environment more or less conducive to rest, such as opening/closing a window, playing loud/soft music, turning on the air conditioner or the heater to high/low.

In some implementations, the system can determine analyze the biological information of the user and determine whether the rest state of the user corresponds to a particular stage of sleep (e.g., deep sleep or light sleep). In some implementations, the system may use a past history of the user to determine the rest state of the user. For example, the system may analyze a past history of the user's sleeping or resting patterns to determine how much time is typically needed by the user for a particular level of rest. In such scenarios, the system may generate a recommendation of rest based on the user's past history to create a personalized and more accurate recommendation of rest.

For example, in some implementations, the system may utilize cumulative life-log data that has been collected from the wearable device worn by the user. The historical data (e.g., life-log data) of a user may be used to personalize the analysis for the user (e.g., the system may account for a user's high average blood pressure, or low average heart rate, etc.). Based on this historical information of the user, the system may determine a drowsy state of the user. For example, the system may detect whether the user has gotten enough sleep, eaten enough, has exercised too much, etc. Based on the user's drowsy state, the system may determine whether the user needs rest. In some implementations, a user's life-log data may itself be utilized to determine the drowsy state of the user and/or the life-log data may be used as a baseline by which other measurements (e.g., measurements taken while the user is driving) may be compared to determine the user's drowsy state.

The system may determine traffic condition based on any suitable information. For example, the system may utilize the vehicle's navigation system, or may utilize a wearable device worn by the user (e.g., to determine speed of travel, or to wirelessly receive traffic information from an external source), or may utilize any suitable technique to determine current traffic conditions. In some implementations, the system may analyze traffic conditions other than current traffic conditions. For example, the system may determine a future expected traffic condition (e.g., by receiving such information from an external source, or by applying predictive algorithms to estimate future traffic conditions, etc.). As another example, the system may generate hypothetical traffic conditions to determine estimated times of arrival for the different hypothetical traffic conditions (e.g., to determine a sensitivity of the system's rest recommendation to varying traffic conditions, etc.).

The system may generate recommendations to rest and/or alarms using various techniques. For example, the recommendation to rest may be in the form of visible information (e.g., an image or text) that is displayed on a display unit of the user's wearable device (e.g., a smart watch) or on a display unit of the vehicle. As another example, the recommendation to rest may be in the form of an audible recommendation, such as a voice output from the user's wearable device or the vehicle's sound system. The alarm may be a visible alarm (e.g., a light), or an audible alarm (e.g., music, or beeping, etc.) or a vibration, and may be output from either the vehicle itself or from a wearable device worn by the user.

Description will now be given in detail according to some implementations disclosed herein, with reference to the accompanying drawings. For the sake of brief description with reference to the drawings, the same or equivalent components may be provided with the same or similar reference numbers, and description thereof will not be repeated. The accompanying drawings are used to help easily understand various technical features and the implementations presented herein are not limited by the accompanying drawings. As such, the present disclosure should be construed to extend to any alterations, equivalents and substitutes in addition to those which are particularly set out in the accompanying drawings.

FIG. 1 is a block diagram of an example of a wearable device.

In this example, the wearable device 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

In the example of FIG. 1, the wearable device 100 is shown having wireless communication unit 110 configured with several commonly implemented components. For instance, the wireless communication unit 110 typically includes one or more components which permit wireless communication between the wearable device 100 and a wireless communication system or network within which the wearable device is located.

The wireless communication unit 110 typically includes one or more modules which permit communications such as wireless communications between the wearable device 100 and a wireless communication system, communications between the wearable device 100 and another wearable device, communications between the wearable device 100 and an external server. Further, the wireless communication unit 110 typically includes one or more modules which connect the wearable device 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

In some implementations, the device 100 may include an information collection unit that is configured to collect information regarding a user's physical condition. In some implementations, the information collection unit may include one or more sensors that directly sense the information regarding the user's physical condition. Additionally or alternatively, in some implementations, the information collection unit may include one or more communication units that receive the information regarding the user's physical condition from another device (e.g., an external sensor). Additionally or alternatively, in some implementations, the information collection unit may include one or more input units that receive the information regarding the user's physical condition as direct input from a user.

In the example of FIG. 1, an information collection unit may be implemented, for example, by the wireless communication unit 110 and/or the input unit 120 and/or the sensing unit 140. For example, the sensing unit 140 is typically implemented using one or more sensors configured to sense internal information of the wearable device, the surrounding environment of the wearable device, user information, and the like. For example, in FIG. 1, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, an ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The wearable device 100 may be configured to utilize information obtained from sensing unit 140, and in particular, information obtained from one or more sensors of the sensing unit 140, and combinations thereof.

In some implementations, the sensing unit 140 may be configured to sense one or more biological signals of a user. For example, the sensing unit may include various sensors (for example, a GSR sensor, a body temperature sensor, a pulse sensor, a pressure sensor, or the like) provided in a body of the wearable device 100.

The biological signal may include various types of information regarding the user (e.g., related to physical activity, sleep, diet, stress, sickness, or other physical conditions or activities) that affect driving ability.

As specific examples, the biological signal may indicate an amount of glucose in the user's blood, which may indicate eating activity by the user. As another example, the biological signal may indicate a heart or pulse rate, indicating sleep or inactivity. As another example, the biological signal may indicate a number of times the user has performed a movement or applied stress to a muscle, which may indicate an exercising movement. Using such examples of biological signals, or others, the sensing unit 140 may collect various types of information that may indicate the user's level of hunger, fatigue, or other physical condition.

The wearable device may also store information related to the user's physical condition, such as the user's age or body weight. Such information may be automatically determined by the wearable device (e.g., based on accessing pre-stored information in other databases) or may be manually entered by the user.

In some implementations, the biological signal refers to an electrical signal generated by the body of the wearer who wears the wearable device 100. For example, the biological signal may be any one of an ECG (ElectroCardioGram) signal, a PPG (Photoplethymogram) signal, and a GSR (Galvanic Skin Response) signal, but the present disclosure is not limited thereto and the biological signal may include any type of signal widely used in the art to measure a sleep stage. For example, a body temperature sensor, a pulse sensor, a pressure sensor, or the like, may additionally or alternatively be included.

As a detailed example, major electrical criteria generated by a body of the wearer may include electro-encephalogram (EEG), electrocardiogram (ECG), an electromyogram (EMG), galvanic skin response, or the like, and major physical criteria includes blood pressure, a heart rate, arrhythmia, a stroke quotient, beat defect, a body temperature, a breathing rate, and the like. At least one or more of the major electrical criteria and major physical criteria may be sensed through sensors provided in the wearable device 100.

In some implementations, an electrocardiogram (ECG) signal is an electrical signal generated from a surface of a skin according to electrical activity of the heart. The ECG signal may be measured by inducing an activity current generated by the heart muscle according to cardiac impulse to two appropriate locations of a body surface.

An electromyogram (EMG) signal is an electrical signal generated from a surface of a skin according to contractile force of muscle, muscle activity, and fatigue of the muscles. EMG may be obtained by sensing a movement of tendons according to a movement of fingers of the wearer sensed when the wearable device 100 is worn. In detail, finger flexor tendons of tendons administering movements of fingers exist in a carpal tunnel within a wrist of the terminal wearer. The finger flexor tendons include nine tendons and one nerve, and when a finger is moved, the nine tendons included in the finger flexor tendons are moved in various combinations. A sensing unit (e.g., the sensing unit 140 in FIG. 1) of the wearable device may sense a shape of the tendons deformed according to a movement of fingers or the wrist, and a controller (e.g., the controller 180 in FIG. 1) may determine which gesture the fingers make based on the sensed information.

The electroencephalogram (EEG) signal is an electrical signal generated from a surface of the skin according to brain activity with respect to concentration or an external stimulus. The EEG signal may be measured by inducing potential fluctuation that occurs in the cerebrum of a person or a brain current generated according to the potential fluctuation from the scalp.

The GSR signal is an electrical signal generated from a surface of the skin according to a change in skin resistance to activity of the sympathetic nerve. The GSR signal may be obtained by measuring a phenomenon that electrical resistance is temporarily reduced, action potential is generated, and the like, due to an external stimulus or emotional excitement in the skin of a living body.

In some implementations, the body sensor periodically detects a temperature of the wrist of the wearer. In this case, when the wearable device 100 is worn on a body part other than on the wrist, a temperature of the body part on which the wearable device 100 is worn is detected. In a case in which the wearable device 100 is worn on a steering wheel of the vehicle, a temperature of the driver's palm holding the steering wheel is periodically detected.

The GSR sensor detects the amplitude of heart beats transmitted through blood and the muscle distributed in the wrist of the wearer and senses a reaction of the body corresponding to a change in an autonomic nerve. Also, in a case in which the wearable device 100 is worn on the steering wheel, for example, a pressure sensor may obtain state information of the driver through a change in pressure (grasping power or grip) of the driver's hand grasping the wheel.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the wearable device 100 and a user, as well as function as the user input unit 123 which provides an input interface between the wearable device 100 and the user.

The interface unit 160 serves as an interface with various types of external devices that can be coupled to the wearable device 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the wearable device 100 may perform assorted control functions associated with a connected external device, in response to the external device being connected to the interface unit 160.

The memory 170 is typically implemented to store data to support various functions or features of the wearable device 100. For instance, the memory 170 may be configured to store application programs executed in the wearable device 100, data or instructions for operations of the wearable device 100, and the like. Some of these application programs may be downloaded from an external server via wireless communication. Other application programs may be installed within the wearable device 100 at time of manufacturing or shipping, which is typically the case for basic functions of the wearable device 100 (for example, receiving a call, placing a call, receiving a message, sending a message, and the like). It is common for application programs to be stored in the memory 170, installed in the wearable device 100, and executed by the controller 180 to perform an operation (or function) for the wearable device 100.

The controller 180 typically functions to control overall operation of the wearable device 100, in addition to the operations associated with the application programs. The controller 180 may provide or process information or functions appropriate for a user by processing signals, data, information and the like, which are input or output by the various components depicted in FIG. 1, or activating application programs stored in the memory 170.

As one example, the controller 180 controls some or all of the components illustrated in FIG. 1 according to the execution of an application program that have been stored in the memory 170. For driving of the application program, the controller 180 may operate the wearable device 100 by combining at least two of the components of the wearable device 100.

The power supply unit 190 can be configured to receive external power or provide internal power in order to supply appropriate power required for operating elements and components included in the wearable device 100. The power supply unit 190 may include a battery, and the battery may be configured to be embedded in the terminal body, or configured to be detachable from the terminal body.

At least part of the components may operate in a cooperating manner, so as to implement an operation, a control, or a control method of a wearable device according to various implementations. The operation, the control, or the control method of the wearable device may be implemented on the wearable device, by driving of at least one application program stored in the memory 170.

Referring to FIG. 1, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some implementations, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external wearable device, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the wearable device 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some implementations, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the wearable device 100 and a wireless communication system, communications between the wearable device 100 and another wearable device 100, or communications between the wearable device and a network where another wearable device 100 (or an external server) is located, via wireless area networks. One example of the wireless area networks is a wireless personal area networks.

In some implementations, another wearable device (which may be configured similarly to wearable device 100) may be a wearable device, for example, a smart watch, a smart glass or a head mounted display (HMD), which is able to exchange data with the wearable device 100 (or otherwise cooperate with the wearable device 100). The short-range communication module 114 may sense or recognize the wearable device, and permit communication between the wearable device and the wearable device 100. In addition, when the sensed wearable device is a device which is authenticated to communicate with the wearable device 100, the controller 180, for example, may cause transmission of data processed in the wearable device 100 to the wearable device via the short-range communication module 114. Hence, a user of the wearable device may use the data processed in the wearable device 100 on the wearable device. For example, when a call is received in the wearable device 100, the user may answer the call using the wearable device. Also, when a message is received in the wearable device 100, the user can check the received message using the wearable device.

The location information module 115 is generally configured to detect, calculate, derive or otherwise identify a position of the wearable device. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the wearable device.

As one example, when the wearable device uses a GPS module, a position of the wearable device may be acquired using a signal sent from a GPS satellite. As another example, when the wearable device uses the Wi-Fi module, a position of the wearable device can be acquired based on information related to a wireless access point (AP) which transmits or receives a wireless signal to or from the Wi-Fi module.

The input unit 120 may be configured to permit various types of input to the wearable device 100. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the wearable device 100. As another example, the cameras 121 may be located in a stereoscopic arrangement to acquire left and right images for implementing a stereoscopic image.

The microphone 122 is generally implemented to permit audio input to the wearable device 100. The audio input can be processed in various manners according to a function being executed in the wearable device 100. If desired, the microphone 122 may include assorted noise removing algorithms to remove unwanted noise generated in the course of receiving the external audio.

The user input unit 123 is a component that permits input by a user. Such user input may enable the controller 180 to control operation of the wearable device 100. The user input unit 123 may include one or more of a mechanical input element (for example, a key, a button located on a front and/or rear surface or a side surface of the wearable device 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the wearable device at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the wearable device, surrounding environment information of the wearable device, user information, or the like. The controller 180 generally cooperates with the sending unit 140 to control operation of the wearable device 100 or execute data processing, a function or an operation associated with an application program installed in the wearable device based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the wearable device covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the wearable device 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some implementations, the controller 180 may execute the same or different controls according to a type of touch object that touches the touch screen or a touch key provided in addition to the touch screen. Whether to execute the same or different control according to the object which provides a touch input may be decided based on a current operating state of the wearable device 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the wearable device 100. For example, the display unit 151 may display execution screen information of an application program executing at the wearable device 100 or user interface (UI) and graphic user interface (GUI) information in response to the execution screen information.

In some implementations, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the wearable device 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the wearable device 100.

An optical output module 154 can output a signal for indicating an event generation using light of a light source. Examples of events generated in the wearable device 100 may include message reception, call signal reception, a missed call, an alarm, a schedule notice, an email reception, information reception through an application, and the like.

A signal output by the optical output module 154 may be implemented in such a manner that the wearable device emits monochromatic light or light with a plurality of colors. The signal output may be terminated as the wearable device senses that a user has checked the generated event, for example.

The interface unit 160 serves as an interface for external devices to be connected with the wearable device 100. For example, the interface unit 160 can receive data transmitted from an external device, receive power to transfer to elements and components within the wearable device 100, or transmit internal data of the wearable device 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various types of information for authenticating authority of using the wearable device 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the wearable device 100 is connected with an external cradle, the interface unit 160 can serve as a passage to allow power from the cradle to be supplied to the wearable device 100 or may serve as a passage to allow various command signals input by the user from the cradle to be transferred to the wearable device there through. Various command signals or power input from the cradle may operate as signals for recognizing that the wearable device is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The wearable device 100 may also be operated in relation to a network storage device that performs the storage function of the memory 170 over a network, such as the Internet.

The controller 180 may typically control the general operations of the wearable device 100. For example, the controller 180 may set or release a lock state for restricting a user from inputting a control command with respect to applications when a status of the wearable device meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various some implementations disclosed herein.

The power supply unit 190 receives external power or provide internal power and supply the appropriate power required for operating respective elements and components included in the wearable device 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various implementations described herein may be implemented in a computer-readable medium, a machine-readable medium, or similar medium using, for example, software, hardware, or any combination thereof.

In some implementations, a wearable device 100 may be configured as a device which is wearable on a human body. Examples of the wearable device 100 include a smart watch, a smart glass, a head mounted display (HMD), and the like. In some implementations, the wearable device 100 may cooperate with another device (e.g., another wearable device, a smart phone, etc.).

As a specific example, the wearable device 100 can exchange data with (or cooperate with) another mobile device (e.g., another wearable device or a smart phone, etc.). In such a scenario, the wearable device 100 may have functionality that is less than the cooperating mobile device. For instance, the short-range communication module 114 of the wearable device 100 may sense or recognize a wearable device that is near-enough to communicate with the cooperating mobile device. In addition, when the sensed mobile device is a device which is authenticated to communicate with the wearable device 100, the controller 180 may transmit data processed in the wearable device 100 to the mobile device via the short-range communication module 114 (or the wearable device 100 may receive data that was processed in the cooperating mobile device), for example. Hence, a user of the cooperating mobile device can use the data processed in the wearable device 100 on the mobile device, or can use data processed in the mobile device on the wearable device 100. For example, when a call is received on the cooperating mobile device (e.g. a smart phone), the user can answer the call using the wearable device 100. As another example, when a message is received on the cooperating mobile device (e.g., a smart phone), the user can check the received message using the wearable device 100.

Figure 2:
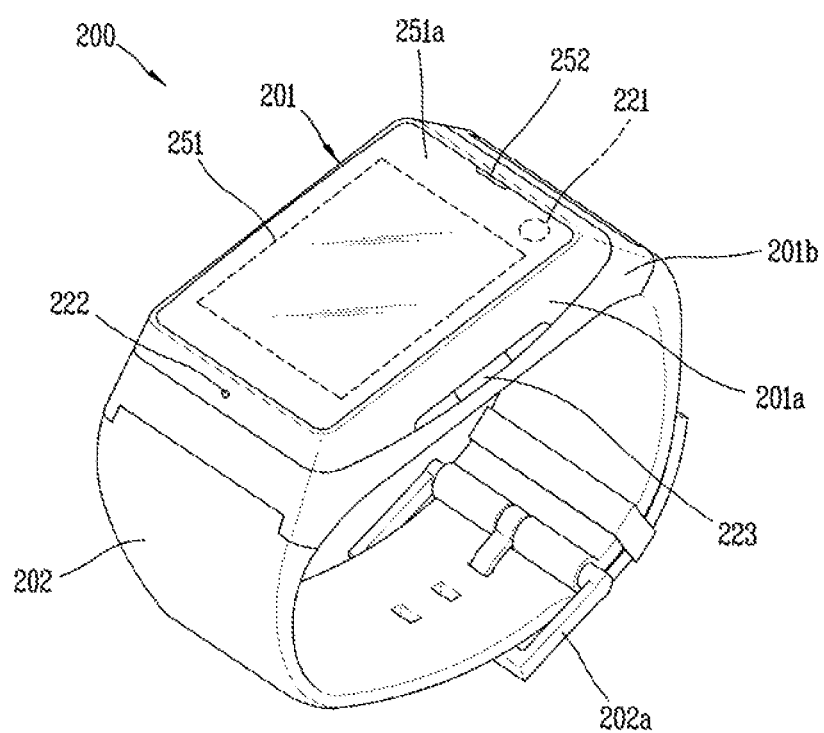
FIG. 2 is a perspective view illustrating an example of a watch-type wearable device.

FIG. 2 is a perspective view illustrating an example of a watch-type wearable device. As illustrated in FIG. 2, the watch-type wearable device 200 includes a main body 201 with a display unit 251 and a band 202 connected to the main body 201 to be wearable on a wrist. In general, wearable device 200 may be configured to include features that are the same or similar to that of wearable device 100 of FIG. 1.

The main body 201 may include a case having a certain appearance. As illustrated, the case may include a first case 201a and a second case 201b cooperatively defining an inner space for accommodating various electronic components. Other configurations are possible. For instance, a single case may alternatively be implemented, with such a case being configured to define the inner space, thereby implementing a wearable device 200 with a uni-body.

The watch-type wearable device 200 can perform wireless communication, and an antenna for the wireless communication can be installed in the main body 201. The antenna may extend its function using the case. For example, a case including a conductive material may be electrically connected to the antenna to extend a ground area or a radiation area.

The display unit 251 is shown located at the front side of the main body 201 so that displayed information is viewable to a user. In some implementations, the display unit 251 includes a touch sensor so that the display unit can function as a touch screen. As illustrated, window 251a is positioned on the first case 201a to form a front surface of the terminal body together with the first case 201a.

The illustrated example includes audio output module 252, a camera 221, a microphone 222, and a user input unit 223 positioned on the main body 201. When the display unit 251 is implemented as a touch screen, additional function keys may be minimized or eliminated. For example, when the touch screen is implemented, the user input unit 223 may be omitted.

The band 202 is commonly worn on the user's wrist and may be made of a flexible material for facilitating wearing of the device. As one example, the band 202 may be made of fur, rubber, silicon, synthetic resin, or the like. The band 202 may also be configured to be detachable from the main body 201. Accordingly, the band 202 may be replaceable with various types of bands according to a user's preference.

In one configuration, the band 202 may be used for extending the performance of the antenna. For example, the band may include therein a ground extending portion (not shown) electrically connected to the antenna to extend a ground area.

The band 202 may include fastener 202a. The fastener 202a may be implemented into a buckle type, a snap-fit hook structure, a Velcro® type, or the like, and include a flexible section or material. The drawing illustrates an example that the fastener 202a is implemented using a buckle.

In some implementations, the watch-type device 200 may include one or more sensors for sensing whether a user is drowsy. For example, the watch-type device 200 may include a sensing unit (e.g., sensing unit 140 in FIG. 1) that includes one or more sensors that detect one or more biological signals of a user. Such sensors may be included on any suitable portion of the watch-type device 200, such as on the main body 201, band 202, or other part of the watch-type device 200. In some implementations, the sensing unit (e.g., sensing unit 140 in FIG. 1), or one or more sensors of the sensing unit, may be physically separate from the main body of the watch-type device 200 and may be communicative (e.g., via wireless communication) with the controller (e.g., controller 180 in FIG. 1) of the watch-type device 200. For example, in some implementations, sensors may include a camera that is remote from the watch-type device 200 (e.g., installed in the vehicle) and communicative with the watch-type device 200 to provide image information regarding the user who wears the watch-type device 200.

Figure 3:
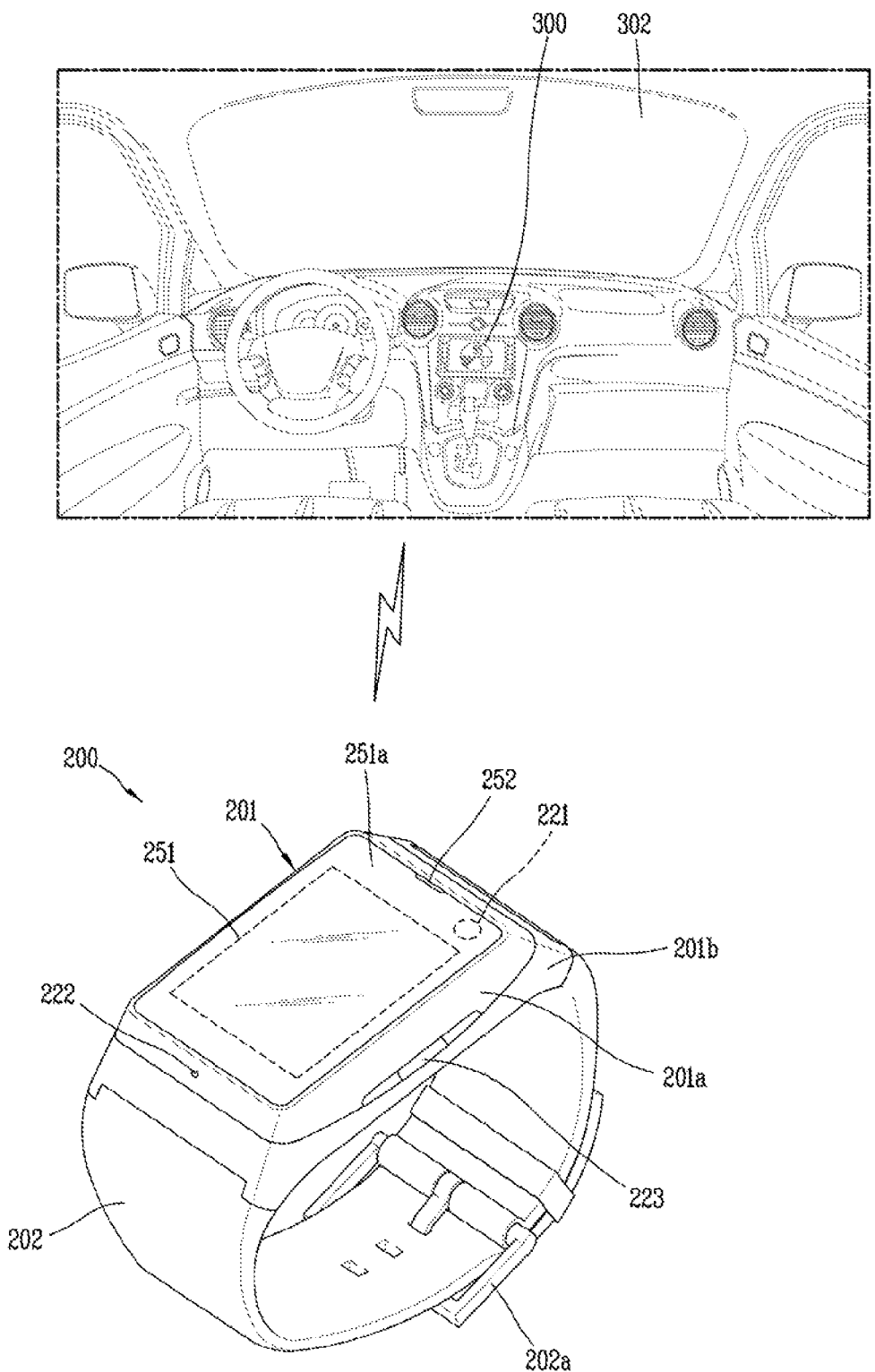
FIG. 3 is sketch illustrating an example of a smart watch operating in conjunction with a vehicle.

FIG. 3 is sketch illustrating an example in which a smart watch interacts with a vehicle.

In the example of FIG. 3, the wearable device 200 may be connected by wire or wireless to a controller (not shown) of a vehicle to request the controller to perform a specific function. The state in which the vehicle interacts with the wearable device 200 by being connected to the wearable device 200 as described above is referred to as a 'connected car' state.

If the state becomes the 'connected car' state as described above, the wearable device 200 may transmit image information and/or sound information output from the wearable device 200 through a predetermined interface to an audio/video (A/V) output device provided in the vehicle. The image information and/or sound information transmitted to the output device of the vehicle as described above may be output through a display unit 300 and/or an audio system (not shown), provided in the vehicle. In this state, the interface for transmitting the image information and/or sound information, for example, may be a means for supporting wireless communication, such as a wireless fidelity (WiFi) transceiver or Bluetooth transceiver, or a means for supporting wire communication, such as a universal serial bus (USB) terminal.

In some implementations, if the state becomes the 'connected car' state, the wearable device 200 may allow at least one of executable functions in the vehicle to be performed. For example, the wearable device 200 may allow image information output in the display unit 251 to be displayed in a head up display (HUD) scheme through the display unit 300 provided in the vehicle or a wind shield glass 302 of the vehicle. Alternatively or additionally, the wearable device 200 may suggest that a user open the window of the vehicle or reproduce specific music data through an interface displayed on the display unit 251 thereof. Alternatively or additionally, the wearable device 200 may allow navigation information related to a predetermined specific point to be displayed on the display unit 300 of the vehicle.

If the state becomes the 'connected car' state, the controller (not shown) of the vehicle may obtain an image of a driver through a camera provided in the vehicle, e.g., a camera mounted inside the vehicle, and transmit the obtained image to the wearable device 200 connected to the vehicle. Then, the wearable device 200 may analyze the obtained image and detect a state in which the driver's head moves and/or a number of times or time when the driver closes eyes. In addition, the wearable device 200 may decide whether the driver is drowsy during driving of the vehicle, using the analyzed image.

Hereinafter, some implementations related to a control method implemented in the wearable device configured as described above will be described with reference to the accompanying drawings. In the following description, the case where a smart watch is used as an example of the wearable device 200 will be described for convenience. However, implementations are not limited thereto.

Figure 4:
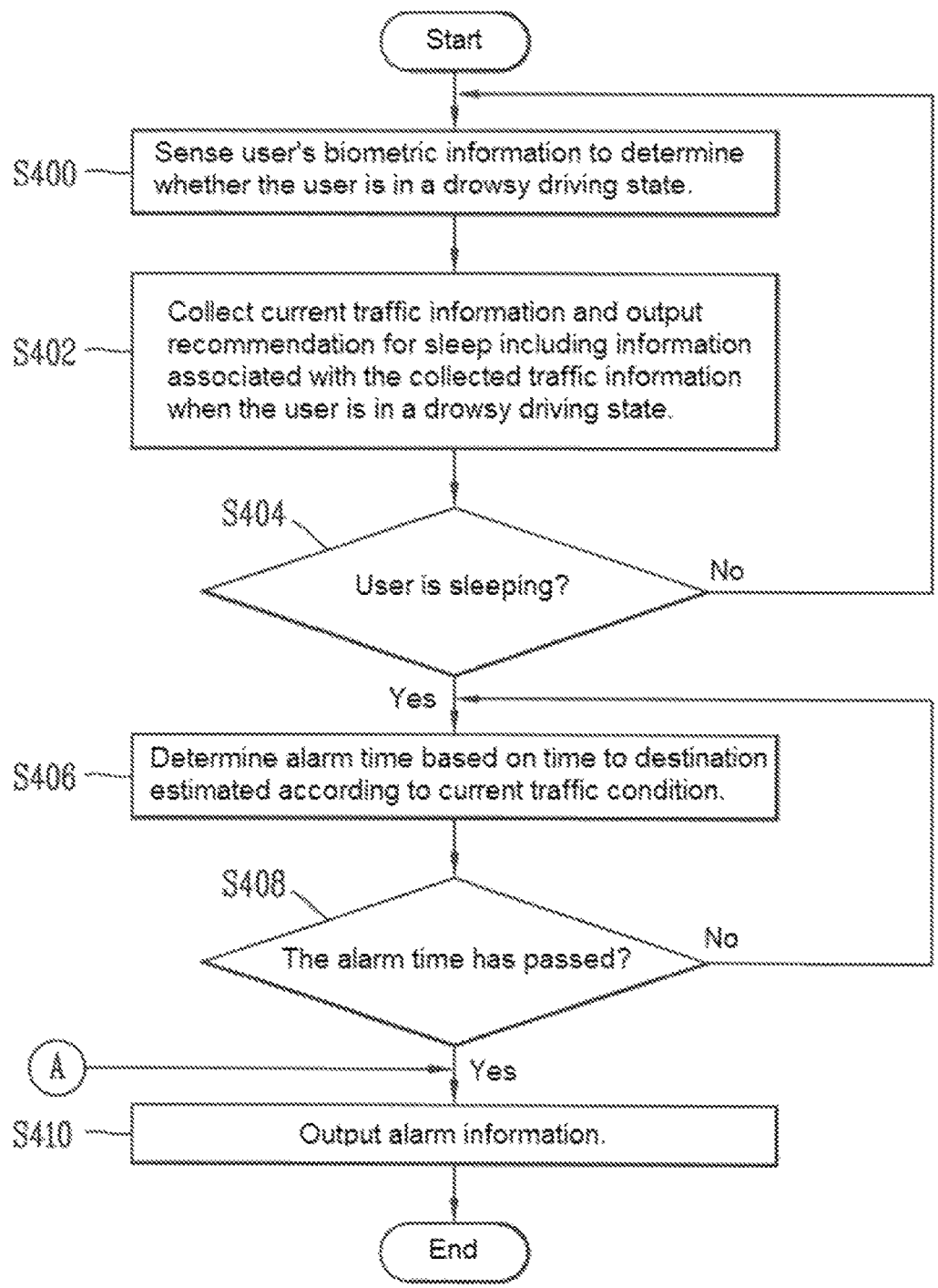
FIG. 4 is a flowchart illustrating an example of an operation of a DSM system.

FIG. 4 is a flow chart illustrating an operation of a DSM system.

Referring to example of FIG. 4, the controller (e.g., controller 180 in FIG. 1) may determine whether or not a user drives a vehicle. Furthermore, if it is determined that the user drives a vehicle, the controller 180 senses the user's biological information to determine whether or not the user is in a drowsy driving state (S400).

For example, if a user rides in a vehicle (e.g., a particular pre-specified vehicle that operates the DSM system) or if a seat occupied by the user is a driver's seat, the controller 180 determines that the user is driving a vehicle. Furthermore, in this state, the controller 180 may determine the user's drowsy driving state in various ways. For example, the controller 180 may determine whether or not the user is in a drowsy driving state using at least one of a result of checking the user's heat rate or a result of sensing the user's temperature change or the user's degree of muscle relaxation, and the like, and determine whether or not there is a danger of drowsy driving even though the user is not in a drowsy driving state.

In some implementations, if the system has determined that the user is in a drowsy driving state in step S400 or a user's drowsy driving possibility is above a preset level, the controller 180 may output image information or audio information for recommending rest to the user (S402).

The image information and/or audio information output in the step S402 may include data for recommending rest to the user. For example, the image information and/or audio information may include information on a current traffic condition collected by the controller 180. In other words, the image information and/or audio information may include information on a driving time to a preset destination and expected arrival time calculated based on the current traffic condition, and a time for driving to the destination and its resultant expected arrival time in a typical case.

In some implementations, if traffic jam or traffic congestion occurs on a path to the currently preset destination, then the controller 180 may notify information on an expected arrival time reflected with the traffic congestion and a result compared with an expected arrival time to the destination in a state that the traffic congestion does not occur.

In some implementations, the controller 180 may collect statistical information on traffic conditions for each hour to estimate a time at which traffic congestion condition to the destination is improved above a predetermined level in advance. Furthermore, the controller 180 may calculate an expected arrival time to the destination based on an expected driving time estimated when the user drives a vehicle at an estimated time.

In some implementations, the controller 180 may provide a result of comparing a case where he or she continuously drives a vehicle with a case where he or she drives a vehicle while avoiding the traffic congestion condition at the estimated time after taking a short break to the user. In some implementations, when the user is in a drowsy driving state or has a high possibility of drowsy driving, the controller 180 may provide a result estimated using information on the collected traffic condition to the user, thereby allowing the user to stop the driving of a vehicle as well as guiding the user to take a break. Hereinafter, an example of image information displayed to recommend rest to the user will be described in more detail with reference to FIG. 7.

In some implementations, the image information and/or audio information output in the step S402 may be output through the audio/video (NV) output unit of the vehicle (which may be mutually linked with a wearable device, such as the smart watch 200 in FIG. 2) or may be output through the wearable device itself. In some implementations, a smart watch may be in a "connected car" state as described above, and the controller 180 may output image information and/or audio information to the vehicle, and the vehicle may output the image information and/or audio information through a preset image information output means and/or an audio information output means in response to the request. Here, the information output means provided in the vehicle may be a display unit of a telematics device (for example, navigation) provided within the vehicle or may be of course at least part of a wind shield glass of the vehicle.

In some implementations, the controller 180 may continue to monitor the user's body status to determine whether the user is in a drowsy driving state or whether the user's drowsy driving state becomes more serious. Furthermore, the controller 180 may check whether or not the user takes a break or sleep based on the determination result (S404).

In the step S404, the controller 180 may determine whether the user gets sleep in a drowsy driving state or the user takes a break according to the recommendation output in the step S402. For example, the controller 180 may determine that the user takes sleep in a drowsy driving state when the vehicle is currently driven, and determine that the user takes a break when the vehicle is in a stopped state for a predetermined period of time. In this case, when determined that the user takes sleep in a drowsy driving state, the controller 180 may immediately output preset audio information, vibration or the like for waking up the user.

In some implementations, when the user is not in a sleeping state in the step S404, the controller 180 proceeds to the step S400 again to sense the user's biological information to determine whether the user is in a drowsy driving state or the user's drowsy driving possibility is above a predetermined level. Furthermore, the controller 180 may output image information and/or audio information for recommending rest to the user in the step S402 based on the determination result of the step S400. Furthermore, if the user's status sensed in the step S400 is changed, then the content of the image information and/or audio information output in the step S402 may be changed based on the changed user's status. In some implementations, when the user is in a more seriously sleeping state, the controller 180 may more strongly recommend the user to take a break through at least one of vibration, audio information with larger volume, and image information with higher brightness.

In some implementations, when the user stops his or her vehicle to take sleep as a result of the determination in the step S404, the controller 180 may determine a time for outputting an alarm or a time for waking up the user (S406). For example, the controller 180 may set the alarm output time based on a preset light sleep time. In some implementations, the light sleep time may be a period of time predetermined by an experiment for finding how long period of light sleep time is most effective to allow the user to avoid drowsy driving state or the like.

In some implementations, the controller 180 may collect information on traffic condition to the destination, and use the collected information to determine the alarm time. In other words, the controller 180 may collect information on traffic condition to the destination in real time or at predetermined intervals, and output an alarm to the user when the traffic condition is improved above a predetermined level.

In some implementations, the controller 180 may determine that the traffic condition has been improved above a predetermined level when there is no points at which congestion of vehicles has occurred on a path to the destination as a result of analyzing information on the collected traffic condition or the congestion of vehicles has occurred below a predetermined level. Otherwise, when an expected arrival time to the destination estimated based on a current traffic condition is within a preset allowed time, the controller 180 may determine that the current traffic condition has been improved above a predetermined level. In some implementations, the preset allowed time may be determined based on an expected arrival time to the destination estimated when traffic congestion does not occur.

Furthermore, when determined that traffic congestion occurs on a path to a preset destination as a result of analyzing information on the currently collected traffic condition, the controller 180 may determine the alarm time based on a difference between a vehicle driving time to the destination in a state that traffic congestion occurs at present and a vehicle driving time to the destination in a state that traffic congestion does not occur.

In some implementations, the controller 180 may use information associated with current traffic condition and traffic condition information for each hour collected to the destination to determine the alarm time. For example, the controller 180 may collect statistical information on traffic condition for each hour to the destination, and estimate a time at which traffic congestion condition to the destination is improved above a predetermined level in advance, and determine a time for outputting the alarm based on the previously estimated time.

In addition, the controller 180 may further consider the user's sleeping status at an alarm time determined in the step S406. For example, the controller 180 may sense the user's heartbeat, and determine whether or not he is in a sleeping status such as REM sleep based on a result of analyzing the user's heartbeat spectrum. In this case, if the user is in a deep sleep as a result of analyzing the sleeping status, then the controller 180 may reflect it to determine a time for outputting the alarm as an alarm time earlier than that determined in the step S406. On the contrary, if the user is in a light sleep, then the controller 180 may reflect it to determine a time for outputting the alarm as an alarm time later than that determined in the step S406.

In some implementations, when the user stops a vehicle to take sleep as a result of the determination in the step S404, the controller 180 may change the internal environment of the vehicle according to the user's sleeping status. For example, the controller 180 may request a change of the internal environment of the vehicle according to the user's sleeping status, and in this case, the controller of the vehicle may change various environmental settings of the vehicle under the control of the controller 180 of the smart watch 100. In some implementations, the environmental settings of the vehicle are previously set to guide the user's sleep, and may be associated with at least any one of illumination, aroma, ventilation status (or air conditioning) inside the vehicle.

In some implementations, when a time for outputting the alarm is determined in the step S406, the controller 180 may check a current time to determine whether or not the determined alarm time has passed (S408). Furthermore, when the alarm time has passed as a result of determining the step S408, the controller 180 outputs alarm information (S410). Here, the controller 180 may output preset vibration or audio information along with image information for the alarm information, and also output the alarm information through the vibration module and the image information and audio information output unit (e.g., mutually linked with a wearable device, such as the smart watch 200 in FIG. 2).

In some implementations, when the alarm time has not passed as a result of determining the step S408, the controller 180 may proceed to the step S406 to determine the alarm time again. In this case, the controller 180 may collect information on traffic conditions again and determine an alarm time again based on the collected information. Accordingly, the alarm time may be changed, and in this case, the controller 180 may compare the changed alarm time with a current time in the step S410 to determine whether or not the current time has passed the alarm time. Furthermore, when the current time is a time that has passed the newly determined alarm time as a result of the determination in the step S410, the controller 180 may proceed to the step S410 to output the alarm information.

In some implementations, when the currently determined alarm time has not passed, the controller 180 may collect traffic information again to output the alarm according to the traffic information. Consequently, the controller 180 may collect information on traffic conditions in real time or at predetermined intervals and reflect it to adjust the user's rest time.

Furthermore, the controller 180 may consider a time at which the user enters an initial sleep state to secure the minimum rest time. For example, when determining an alarm time, the controller 180 may determine a time for outputting the alarm to a time subsequent to a time point at which the preset minimum rest time has passed.

In some implementations, when the alarm is output, the controller 180 may sense the user's body status again to determine whether or not the user's rest time is further required. In this case, the controller 180 may display a result of sensing the user's body status through image information or the like, and notifies that he or she further needs rest, and display image the information and/or audio information for recommending rest to the user again.

In some implementations, the controller 180 may collect information on traffic conditions to the destination, and allow it to be included in the image information and/or audio information for recommending rest. Accordingly, the image information and/or audio information may include a result of comparing an expected arrival time to a preset destination calculated according to a current traffic condition with an expected arrival time to the destination after the user takes a predetermined break time calculated based on traffic condition statistics information for each hour to the destination as described in the step S402.

In some implementations, as a result of the determination in the step S404, the controller 180 may search whether or not there is a prestored schedule affected by the rest. For example, the prestored schedule may be a meeting or appointment according to a calendar, etc. In some implementations, when the user leaves at the alarm time determined in the step S406, the controller 180 may estimate an expected arrival time to a preset destination. Furthermore, the controller 180 may determine whether or not the schedule is affected by the user's rest based on the estimated time. Furthermore, if there is a schedule affected by the user's rest, then the controller 180 may transmit a message to a person related to the schedule (e.g., informing the person that the user will be delayed, as well as, in some examples, additional details regarding the delay such as an amount of delay and/or cause of the delay).

Figure 5:
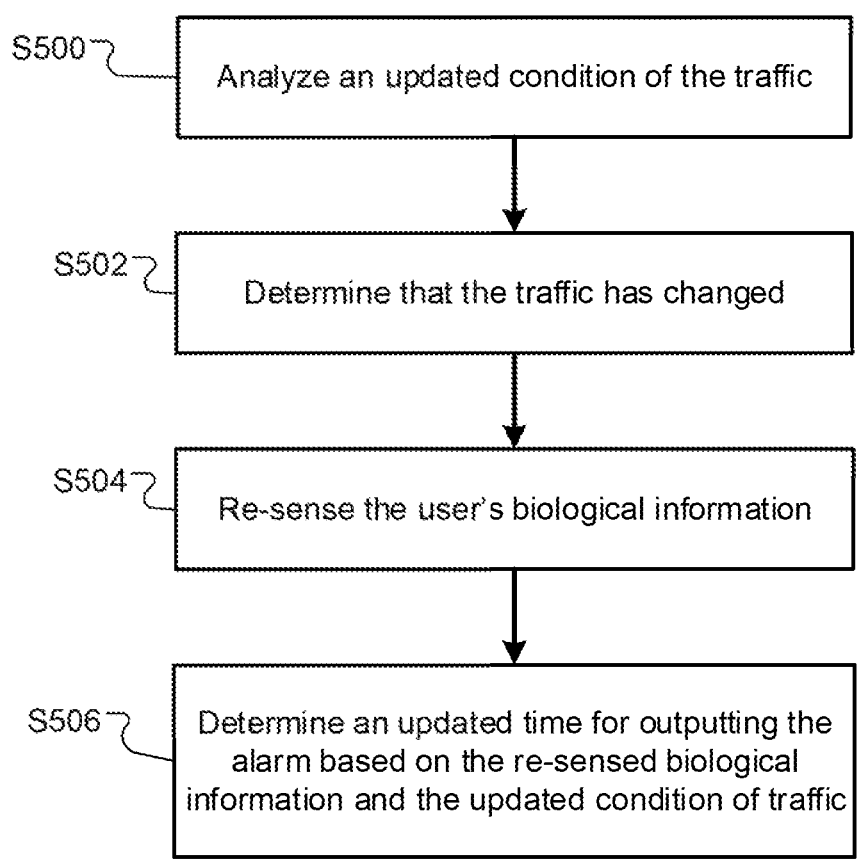
FIG. 5 is a flowchart illustrating another example of an operation of a DSM system.

FIG. 5 is a flowchart illustrating another example of an operation of a DSM system. In this example, the controller (e.g., controller 180 in FIG. 1) performs dynamic adjustment of an alarm time based on updated traffic conditions and updated biological information from a user.

In this example, the controller 180 receives updated condition of the traffic, and analyzes the updated condition in step S500. The updated condition may have been received, for example, either by periodic monitoring of traffic or by a particular criteria that was satisfied to prompt receiving an updated condition of the traffic. Based on analyzing the updated condition of the traffic, the controller 180 determines that the traffic condition has changed, in step S502. For example, the controller 180 may determine that the traffic has gotten more congested or less congested.

In some implementations, the controller 180 may adjust the alarm time based on the updated traffic condition alone. For example, if the controller 180 determines in step S502 that the traffic has become more (or less) congested, then the controller may move the alarm time to an earlier (or later) time, to help ensure that the driver reaches the destination on time while receiving sufficient rest. In some examples, other factors may be taken into consideration. For example, if the system determines that the traffic is extremely congested (e.g., beyond a threshold level of congestion), then the system may determine that leaving earlier would not make an appreciable difference to the time of arrival, and therefore instead of moving the alarm to an earlier time, the system may instead maintain the same alarm time, or may even delay the alarm time.

In some implementations, in addition to the updated traffic condition determined in step S502, the controller 180 may additionally re-sense the user's biological condition, in step S504. This may, for example, enable the system to determine whether the user has already received sufficient rest or whether the user has not received sufficient rest.

Based on the re-sensed biological information and the updated traffic condition, the system may determine a time for outputting the alarm, in step S506. For example, if the system determines that the traffic has become less congested but that the user still has not received sufficient rest, then the system may maintain the same alarm time or may delay the alarm time. As another example, if the system determines that the user has received sufficient rest, then the system may move the alarm time earlier, regardless of traffic condition. For example, the system may try to prevent the user from entering into a deep sleep, and thus may output the alarm at an earlier time to awake the user before the user enters into a deep sleep stage.

In some implementations, instead of adjusting the alarm time, the system may output the alarm as regularly scheduled, and instead provide an updated recommendation to the user. This may be desirable, for example, in scenarios where the user desires greater control over the rest time, rather than allowing the DSM system to adjust the alarm autonomously. In some implementations, after an alarm has been output, the controller 180 may re-sense the biological information of the user, and output updated information recommending rest based on a result of re-sensing the biological-information of the user.

For example, in some scenarios, even after the driver of a vehicle has rested according to the DSM system's recommended rest time, when the alarm is output and the user is awoken, the user may not be sufficiently rested. The DSM system may detect this condition based on re-sensing the user's biological information, and may provide further recommendations that the user rest an additional period of time.

Figure 6:
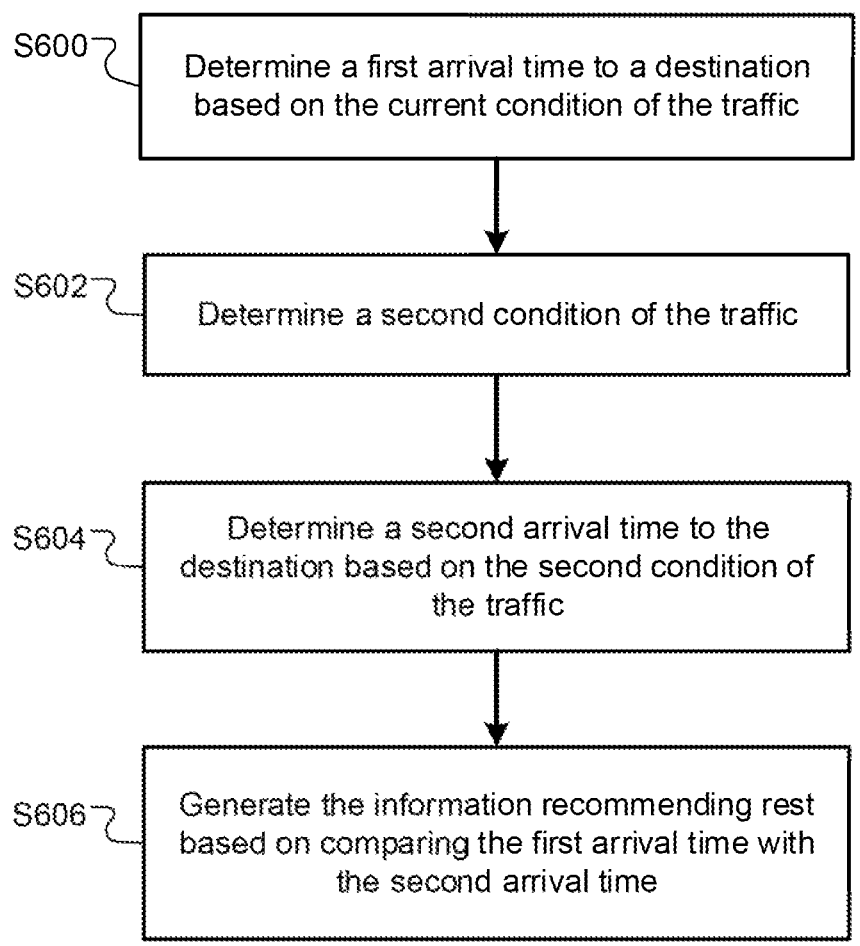
FIG. 6 is a flowchart illustrating another example of an operation of a DSM system.

FIG. 6 is a flowchart illustrating another example of an operation of a DSM system. In this example, the controller (e.g., controller 180 in FIG. 1) determines the recommended rest based on comparing a time of arrival for two different traffic conditions.

In this example, the controller 180 determines a first arrival time to a destination based on the current condition of the traffic, in step S600. The controller 180 then determines a second condition of the traffic, in step S602. The second condition of the traffic may be, for example, a predicted future condition of the traffic, or it may be an estimated alternate condition of the traffic based on uncertainty of measuring the current condition of traffic. In general, the second condition of traffic may be generated according to a variety of techniques to provide additional analysis to the current measured condition of traffic.

The controller 180 may, in step S604, then determine a second arrival time to the destination based on the second condition of the traffic. The controller 180 may then compare the first arrival time with the second arrival time to generate the information recommending rest.

As an example, the controller 180 may generate a second traffic condition as being a more congested traffic condition, and determine that the second time of arrival in this more congested condition would not be much later than in the current traffic condition. In this case, the controller 180 may recommend a greater rest time, as the delay cost of additional rest is outweighed by the benefits of reducing drowsiness. As another example, the controller 180 may generate a second traffic condition that is less congested than the current traffic condition, and may estimate that the second time of arrival in this less congested condition is much sooner than in the current traffic condition. In this case, the controller 180 may recommend a shorter rest time, as the delay benefit of arriving much earlier is outweighed by the negligible additional rest.

FIG. 7 is a sketch illustrating an example of image information for guiding a user to take a break based on a current traffic condition according to an embodiment of the present disclosure.

Referring to the example of FIG. 7, the controller 180 of the smart watch 100 according to an embodiment of the present disclosure may display the image information in a head-up display manner on the display unit 151 provided in the smart watch 100 as well as on the display unit 151 provided in a telematics device (for example, navigation) of the vehicle mutually linked thereto or on a wind shield glass of the vehicle.

Figure 7A:
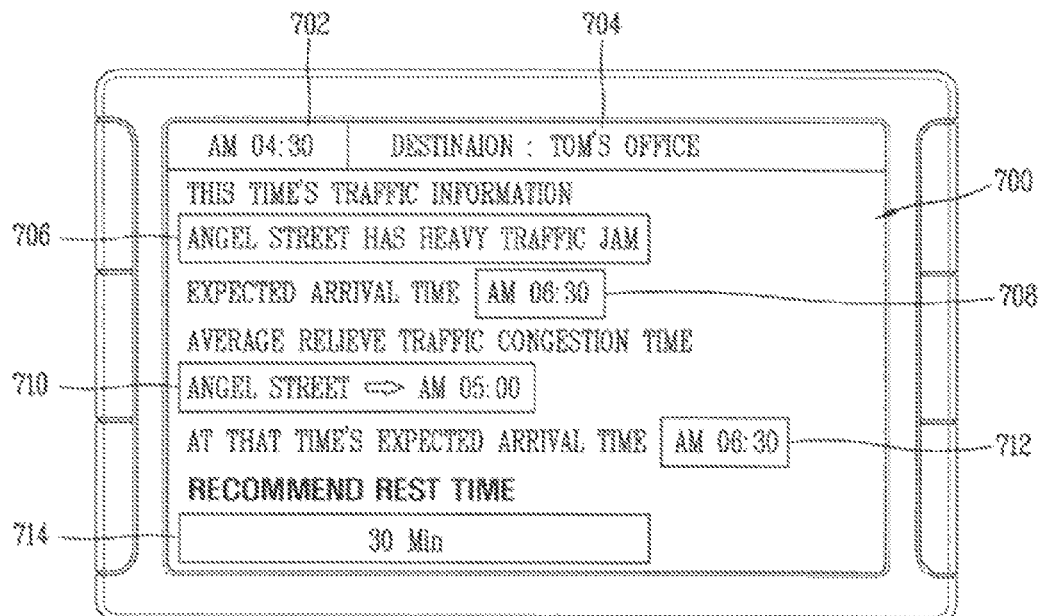
FIGS. 7(A) and 7(B) are diagrams illustrating examples of image information displayed to recommend rest to the user.

First, referring to FIG. 7A, FIG. 7A illustrates an example in which image information for recommending rest to the user is displayed on a display unit provided in the navigation of the vehicle.

As illustrated in FIG. 7A, a current time 702 and information 704 on currently set destination may be displayed on the image information 700 displayed to recommend rest to the user according to an embodiment of the present disclosure, and the image information 700 may include information 706 on a current traffic condition. Moreover, the image information 700 may include information on an expected arrival time 708 expected to the set destination 704 based on the current traffic condition. Accordingly, the user may recognize that traffic congestion has occurred up to the set destination, and check its resultant expected arrival time in advance.

On the other hand, the controller 180 may further display information 710 on a time estimated to improve or relieve traffic congestion that has currently occurred above a predetermined level. Here, the information 710 on a time estimated to improve or relieve the traffic congestion above a predetermined level may be of course obtained from statistical information on traffic conditions for each hour on a path to the destination collected from the information providing center 300.

Furthermore, the controller 180 may display an expected arrival time 712 to the destination estimated when the user leaves at a time at which traffic congestion is relieved on the image information 700. Consequently, according to the present disclosure, it may be possible to compare a case where the user continuously drives a vehicle now while traffic congestion is serious is compared with a case where the user drives a vehicle after traffic congestion is relieved.

As a result, according to the present disclosure, an expected arrival time based on a current traffic condition may be compared with an expected time to arrive at the destination after the user takes a break for a predetermined period of time, thereby guiding the user to take a break without simply displaying a result of sensing the user's body status.

Moreover, the controller 180 may calculate an optimal break time 714 for the user to display the time as illustrated in FIG. 7A. Here, the calculated break time may be determined based on the preset optical light break time or determined based on a difference between an expected arrival time estimated according to a current traffic condition and an expected arrival time to the destination estimated in a state that traffic congestion does not occur. Otherwise, the break time may be calculated based on a current time or a time estimated to relieve the traffic congestion. Furthermore, the controller 180 may output an alarm based on the calculated break time 714, the changed state of the traffic condition and/or the user's sleeping status according to the user's selection.

Figure 7B:
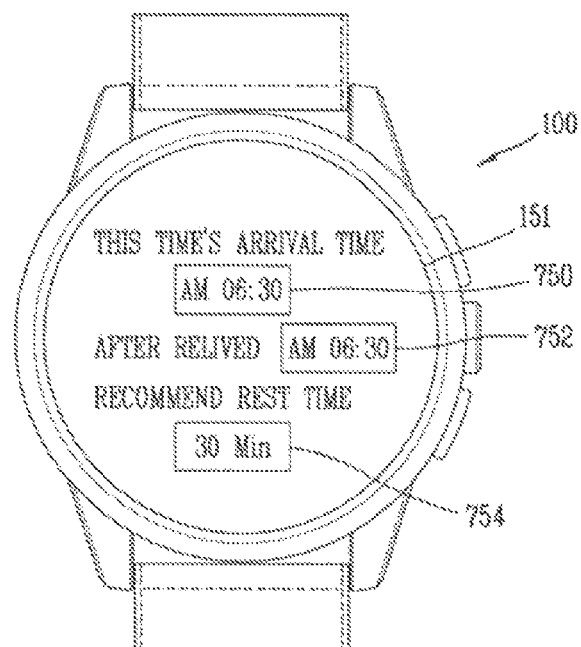

On the other hand, the image information 700 may be also displayed on the display unit 151 of the smart watch 100. FIG. 7B illustrates such an example.

Referring to FIG. 7B, the controller 180 may take a limited area of the display unit 151 of the smart watch 100 into consideration to display information shown in FIG. 7A in summary. For example, information 750 on an expected arrival time estimated based on a current traffic condition and information 752 on an expected arrival time estimated when traffic congestion is relieved may be shown on image information 756 displayed on the display unit 151 of the smart watch 100.

Furthermore, though it is not illustrated in FIG. 7B, the image information 756 displayed on the smart watch 100 may further include information on a current time, information on traffic condition from the current time to the destination, and information on a time estimated to relieve the traffic condition. In addition, the image information 756 may further include information 754 on a break time that can be calculated based on a current time and a time estimated to relieve the traffic condition.

Various implementations may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the wearable device.

The foregoing implementations and advantages are merely examples and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of some implementations described herein may be combined in various ways to obtain additional and/or alternative implementations.

As the present features may be embodied in several forms without departing from the characteristics thereof, it should also be understood that the above-described implementations are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

The methods, techniques, systems, and apparatuses described herein may be implemented in digital electronic circuitry or computer hardware, for example, by executing instructions stored in tangible computer-readable storage media.

Apparatuses implementing these techniques may include appropriate input and output devices, a computer processor, and/or tangible computer-readable storage media storing instructions for execution by a processor.

A process implementing techniques disclosed herein may be performed by a processor executing instructions stored on a tangible computer-readable storage medium for performing desired functions by operating on input data and generating appropriate output. Suitable processors include, by way of example, both general and special purpose microprocessors. Suitable computer-readable storage devices for storing executable instructions include all forms of non-volatile memory, including, by way of example, semiconductor memory devices, such as Erasable Programmable Read-Only Memory (EPROM), Electrically Erasable Programmable Read-Only Memory (EEPROM), and flash memory devices; magnetic disks such as fixed, floppy, and removable disks; other magnetic media including tape; and optical media such as Compact Discs (CDs) or Digital Video Disks (DVDs). Any of the foregoing may be supplemented by, or incorporated in, specially designed application-specific integrated circuits (ASICs).

Although the operations of the disclosed techniques may be described herein as being performed in a certain order and/or in certain combinations, in some implementations, individual operations may be rearranged in a different order, combined with other operations described herein, and/or eliminated, and desired results still may be achieved. Similarly, components in the disclosed systems may be combined in a different manner and/or replaced or supplemented by other components and desired results still may be achieved.

What is claimed is:

1. A driver state monitoring (DSM) system comprising:
a sensing unit configured to sense biological information of a user of a vehicle; and
a controller configured to:
determine a drowsy state of the user based on the sensed biological information;
determine a traffic condition to a destination;
output information recommending rest for the user based on the determined drowsy state of the user and the determined traffic condition to the destination;
monitor the traffic condition to the destination and a rest state of the user based on the user stopping the vehicle in accordance with the information recommending rest;
generate a time at which to output an alarm based on monitoring the traffic condition to the destination and the rest state of the user; and
output the alarm at the generated time.

2. The DSM system of claim 1, wherein the controller is further configured to determine a driving time to the destination, and wherein providing output information recommending rest for the user is based on the driving time and the traffic condition to the destination.

3. The DSM system of claim 1, wherein the controller is further configured to:
detect that the user is in the rest state;
determine an updated traffic condition; and
change the time at which the alarm is to be output based on the updated traffic condition.

4. The DSM system of claim 3, wherein the controller is further configured to, based on analyzing the updated traffic condition, change the time at which to output the alarm based on determining that the updated traffic condition has improved above a predetermined level.

5. The DSM system of claim 3, wherein the controller is further configured to:
re-sense the biological information of the user based on determining that the traffic condition has changed as a result of analyzing the updated traffic condition; and
determine the time at which to output the alarm further based on the re-sensed biological information.

6. The DSM system of claim 1, wherein the controller is further configured to:
re-sense the biological information of the user based on the output of the alarm; and
output updated information recommending rest for the user based on a result of re-sensing the biological information of the user.

7. The DSM system of claim 6, wherein the updated information recommending rest for the user further comprises information associated with an updated drowsy state of the user determined based on the re-sensed biological information of the user.

8. The DSM system of claim 1, wherein the biological information is associated with a heartbeat spectrum of the user, and the controller is further configured to classify the rest state of the user as any one of a plurality of sleep stages based on a result of analyzing the heartbeat spectrum.

9. The DSM system of claim 8, wherein the controller is further configured to determine the time at which to output the alarm based on the classified sleep stage.

10. The DSM system of claim 1, wherein the controller is further configured to, based on the information recommending rest for the user, change an environment inside the vehicle according to preset vehicle environment setting information,
wherein the preset vehicle environment setting information is preset to induce the user to sleep, and is associated with at least one of illumination, aroma, or ventilation inside the vehicle.

11. The DSM system of claim 1, wherein the controller is further configured to:
  determine a first arrival time to the destination based on the traffic condition;
  determine a second traffic condition to the destination;
  determine a second arrival time to the destination based on the second traffic condition to the destination; and
  generate the information recommending rest for the user based on comparing the first arrival time with the second arrival time.

12. The DSM system of claim 11, wherein the controller is further configured to:
  determine an estimated driving time to the destination based on the user resting until the time at which to output the alarm; and
  determine the information recommending rest based on the estimated driving time.

13. The DSM system of claim 1, further comprising a wearable device that is configured to be linked with the vehicle, and
  wherein the controller is further configured to output the information recommending rest for the user on at least one of a display unit of the wearable device or an information display device provided in the vehicle.

14. The DSM system of claim 1, wherein the controller is further configured to output the alarm by outputting at least one of image information, an audible sound, or a vibration.

15. The DSM system of claim 11, wherein the second traffic condition to the destination has less traffic congestion than the traffic condition to the destination.

16. The DSM system of claim 15, wherein the controller is further configured to:
  determine the traffic condition to the destination at a plurality of times while the vehicle is being driven to the destination; and
  determine the second arrival time to the destination based on determining the traffic condition to the destination at the plurality of times.

17. The DSM system of claim 1, wherein the controller is further configured to, based on determining that the user is in a sleep state, determine the time at which to output the alarm further based on a time specified in a preset schedule and based on a driving time to the destination.

18. The DSM system of claim 17, wherein the controller is further configured to, based on determining that the user is in a sleep state:
  determine whether the user is able to arrive at the destination by the time specified in the preset schedule according to the traffic condition to the destination;
  determine contact information associated with the preset schedule; and
  transmit a message using the contact information.

19. The DSM system of claim 1, wherein the controller is further configured to determine a time for outputting the alarm based on a preset light sleep time.

20. A control method of a driver state monitoring (DSM) system, the method comprising:
  sensing biological information of a user of a vehicle, and determining a drowsy state of the user based on the sensed biological information;
  determining a traffic condition to a destination;
  outputting information recommending rest for the user based on the determined drowsy state of the user and the traffic condition to the destination;
  monitoring the traffic condition to the destination and a rest state of the user based on the user stopping the vehicle to take a rest in accordance with the information recommending rest;
  generating a time at which to output an alarm based on monitoring the traffic condition to the destination and the rest state of the user; and
  outputting the alarm at the generated time.

* * * * *